(12) United States Patent
Doe et al.

(10) Patent No.: US 10,161,843 B2
(45) Date of Patent: Dec. 25, 2018

(54) MAINTAINING A MEASUREMENT GAP IN A RHEOMETER

(71) Applicant: Waters Technologies Corporation, Milford, MA (US)

(72) Inventors: Nigel Doe, Wilmington, DE (US); Peter Foster, Avondale, PA (US)

(73) Assignee: WATERS TECHNOLOGIES COPRORATION, Milford, MA (US)

( * ) Notice: Subject to any disclaimer, the term of this patent is extended or adjusted under 35 U.S.C. 154(b) by 226 days.

(21) Appl. No.: 15/397,388

(22) Filed: Jan. 3, 2017

(65) Prior Publication Data

US 2017/0184481 A1 Jun. 29, 2017

Related U.S. Application Data

(63) Continuation of application No. 14/238,043, filed as application No. PCT/US2012/049469 on Aug. 3, 2012, now Pat. No. 9,534,996.

(Continued)

(51) Int. Cl.
*G01N 11/00* (2006.01)
*G01N 11/14* (2006.01)
*G01N 11/04* (2006.01)

(52) U.S. Cl.
CPC .......... *G01N 11/142* (2013.01); *G01N 11/04* (2013.01); *G01N 11/14* (2013.01); *G01N 2011/0006* (2013.01); *G01N 2011/0013* (2013.01)

(58) Field of Classification Search
CPC ......... G01N 1/142; G01N 11/14; G01N 11/04

(Continued)

(56) References Cited

U.S. PATENT DOCUMENTS

| 3,681,980 A | 8/1972 | Decker |
| 4,750,272 A * | 6/1988 | Caddell ................. B23Q 17/22 33/201 |

(Continued)

FOREIGN PATENT DOCUMENTS

| GB | 2356937 A | 6/2001 |
| JP | 2000509502 A | 7/2000 |
| JP | 2004-316713 A | 11/2004 |
| JP | 2009-236924 A | 10/2009 |

OTHER PUBLICATIONS

Extended European Search Report for Application No. 12823999.3, dated Feb. 3, 2015 (8 pages).

(Continued)

*Primary Examiner* — John Fitzgerald
*Assistant Examiner* — Rodney T Frank
(74) *Attorney, Agent, or Firm* — Schmeiser, Olsen & Watts LLP

(57) ABSTRACT

A rheometer includes a drive shaft, a drag cup motor for rotating the drive shaft, a first measuring object supported by the drive shaft, a second measuring object, a linear position sensor, and processing and control electronics. The linear position sensor includes a target (e.g., an aluminum target) mounted to the drive shaft, and a pair of coils. The linear position sensor is configured to measure thermal expansion of the drive shaft based on a change in impedance of the coils resulting from a displacement of the target relative to the coils. The processing and control electronics are in communication with the coils and are configured to adjust a position of one of the measuring objects relative to the other based on a change in impedance of the coils resulting from a displacement of the target relative to the coils, thereby to maintain a substantially constant measurement gap therebetween.

5 Claims, 3 Drawing Sheets

Related U.S. Application Data

(60) Provisional application No. 61/522,871, filed on Aug. 12, 2011.

(58) Field of Classification Search
USPC .......................................................... 73/54.02
See application file for complete search history.

(56) References Cited

U.S. PATENT DOCUMENTS

| | | | |
|---|---|---|---|
| 4,943,771 | A | 7/1990 | Fuschetto |
| 5,077,635 | A * | 12/1991 | Bollhagen ............ G01D 5/2412 |
| | | | 318/662 |
| 6,167,752 | B1 | 1/2001 | Raffer |
| 6,798,099 | B1 | 9/2004 | Doe |
| 7,021,123 | B2 | 4/2006 | Wallevik et al. |
| 7,441,442 | B2 | 10/2008 | Morgan |
| 9,534,996 | B2 | 1/2017 | Doe et al. |
| 2005/0247115 | A1 | 11/2005 | Grey et al. |
| 2007/0151330 | A1 | 7/2007 | Grey et al. |
| 2008/0110246 | A1 | 5/2008 | Old et al. |
| 2010/0269571 | A1 | 10/2010 | Raffer |
| 2014/0202236 | A1 | 7/2014 | Doe et al. |

OTHER PUBLICATIONS

International Search Report and Written Opinion for PCT/US2012/049469, dated Oct. 16, 2012, pp. 9.
Japanese Office Action for Application No. 2014-525073, dated Jun. 28, 2016 (8 pages).

\* cited by examiner

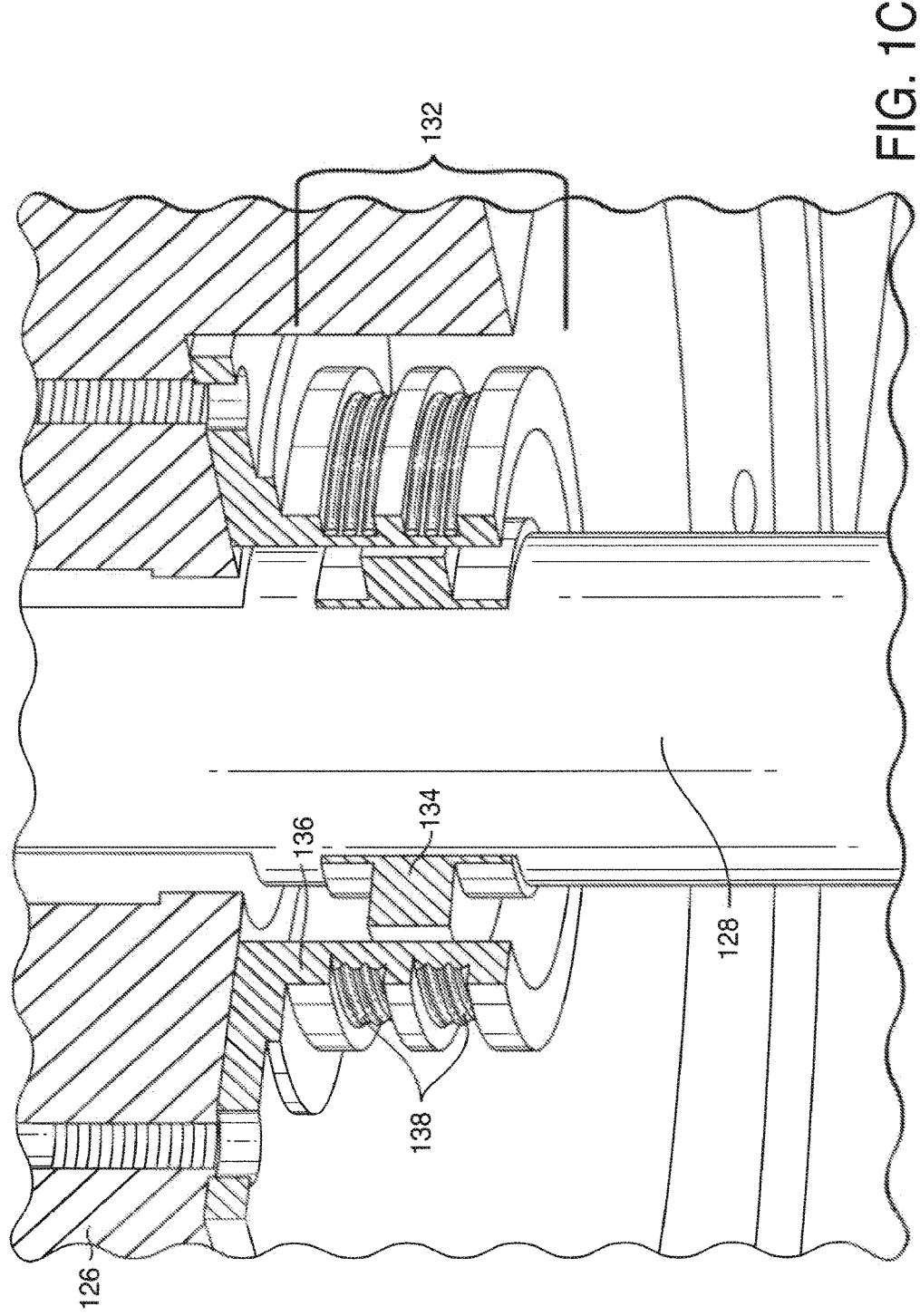

MAINTAINING A MEASUREMENT GAP IN A RHEOMETER

CROSS-REFERENCE TO RELATED APPLICATIONS

This application is a continuation of U.S. patent application Ser. No. 14/238,043, filed on Feb. 10, 2014. U.S. patent application Ser. No. 14/238,043 is the National Stage of International Application No. PCT/US2012/049469, filed Aug. 3, 2012. International Application No. PCT/US2012/049469 claims the benefit of U.S. Provisional Application No. 61/522,871, filed Aug. 12, 2011. The entire contents of these applications are expressly incorporated herein by reference.

TECHNICAL FIELD

This disclosure relates to maintaining a measurement gap in a rheometer, and, more particularly, to correcting changes in a measurement gap associated with thermal expansion of a rheometer drive shaft.

BACKGROUND

Rotary rheometers, viscometers or viscosimeters are used to measure fluid or other properties of materials such as their viscosity by rotating, deflecting or oscillating a measuring object in a material, and measuring, for example, the torque required to rotate or deflect or oscillate the object within the material.

SUMMARY

The invention arises, in part, from the realization that a rheometer can be provided with a position sensor for measuring thermal expansion of a drive shaft such that changes to a measurement gap can be detected and corrected in real time.

In one aspect, the invention provides a rheometer that includes a drive shaft,
a drag cup motor for rotating the drive shaft, a first measuring object supported by the drive shaft, a second measuring object, a linear position sensor, and processing and control electronics. The linear position sensor includes a target (e.g., an aluminum target) mounted to the drive shaft, and a pair of coils. The linear position sensor is configured to measure thermal expansion of the drive shaft based on a change in impedance of the coils resulting from a displacement of the target relative to the coils. The processing and control electronics are in communication with the coils and are configured to adjust a position of one of the measuring objects relative to the other based on a change in impedance of the coils resulting from a displacement of the target relative to the coils, thereby to maintain a substantially constant measurement gap therebetween.

In another aspect, the invention features a method of maintaining a measurement gap in a rheometer. The method includes delivering a high frequency signal to a pair of coils, thereby to set up eddy currents in a target disposed between the coils; measuring impedance in the coils thereby to detect a displacement of the target relative to the coils corresponding to thermal expansion of a drive shaft; and automatically adjusting a position of a first measuring object relative to a second measuring object to maintain a substantially constant measurement gap therebetween.

Implementations may include one or more of the following features.

In some implementations, the coils are mounted for movement relative to the second measuring object.

In certain implementations, the coils are mounted to the drag cup motor.

In some cases, the rheometer also includes a frame and a rheometer head assembly. The frame supports the second measuring object. The rheometer head assembly includes the drag cup motor, the drive shaft, and the linear position sensor, and is mounted for movement relative to the frame. The processing and control electronics are configured to adjust a position of the rheometer head assembly relative to the frame based on a change in impedance of the coils resulting from a displacement of the target relative to the coils, corresponding to thermal expansion of the drive shaft, thereby to maintain a substantially constant measurement gap between the first and second measuring objects.

In some implementations, an impedance of the coils is balanced when the target is centered therebetween.

In certain implementations, the coils are disposed circumferentially about the target.

In some implementations, the measuring objects may be made of, for example, stainless steel, anodized aluminum or titanium.

As used herein, the term "rheometer" shall mean rheometers, viscometers, viscosimeters and similar instruments that are used to measure the properties of fluid or similar materials.

The term "measuring object" shall mean an object having any one of several geometries, including, for example, cones, discs, vanes, parallel plates, concentric cylinders and double concentric cylinders.

Implementations can provide one or more of the following advantages.

In some implementations, a substantially constant measurement gap can be maintained in parallel plate/cone, plate/plate, and/or concentric cylinder measurements.

In certain implementations, measurement gap changes associated with thermal expansion are corrected in real time.

In some implementations, thermal expansion errors are reduced (e.g., eliminated) with the need for special high inertia iron coil former measuring geometries or special environmental system configurations with limited temperature ranges.

Other aspects, features, and advantages are in the description, drawings, and claims.

BRIEF DESCRIPTION OF THE DRAWINGS

FIG. 1C is a schematic perspective view of a position sensor of the rotary rheometer of FIG. 1A.

Like reference numbers indicate like elements.

DETAILED DESCRIPTION

Figure 1A:
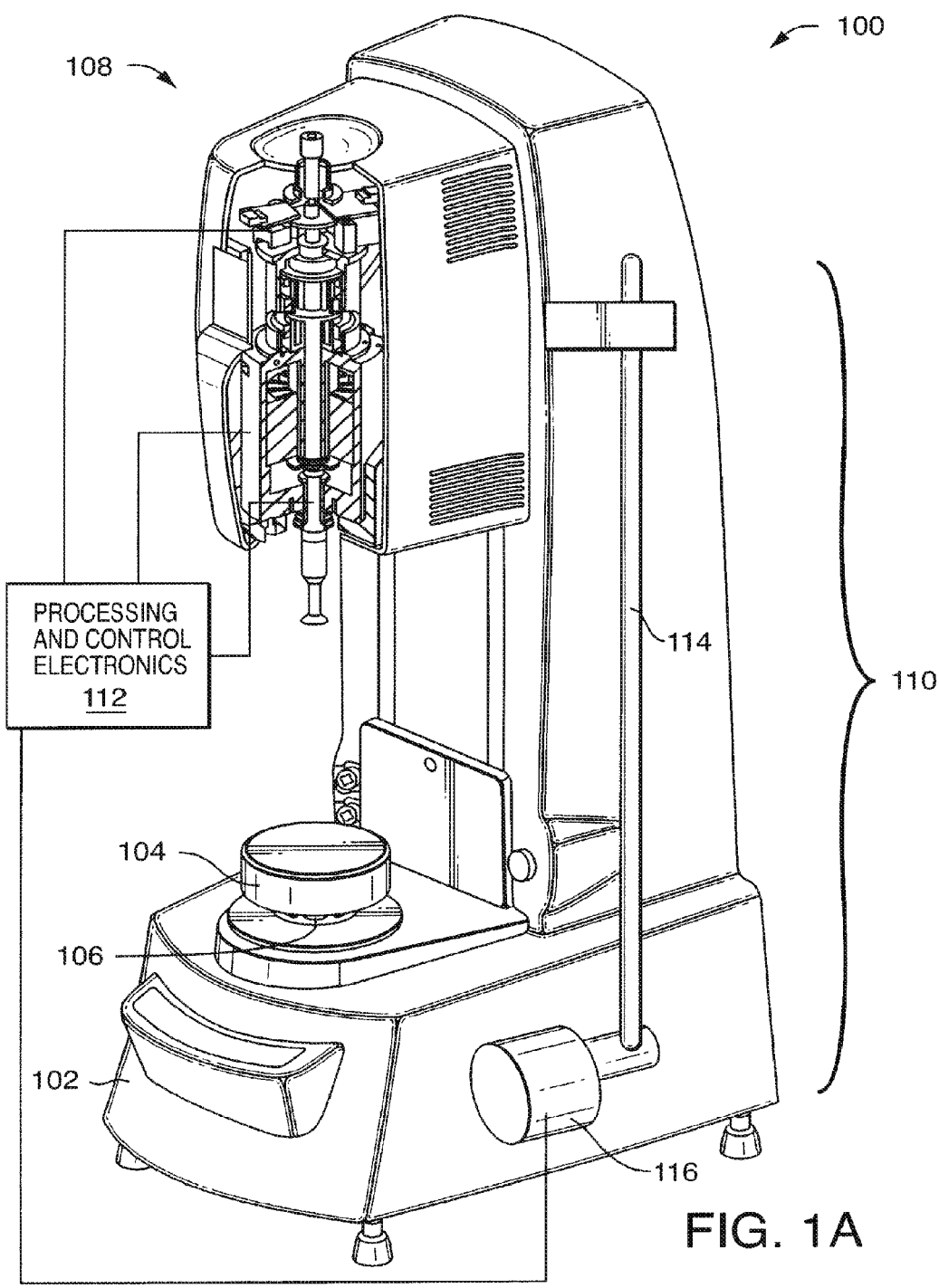
FIG. 1A is a schematic perspective view of a rotary rheometer.

FIG. 1A is a schematic perspective view of a rotary rheometer 100. The rotary rheometer 100 includes a frame 102 (e.g., a single-piece aluminum casting), a first measuring object 104 (shown in the form of a measurement plate) supported by the frame 102, a normal force transducer 106, a rheometer head assembly 108 mounted for movement relative to the frame 102, a linear drive system 110 for controlling movement of the rheometer head assembly 108 relative to the frame 102, and processing and control electronics 112, which, among other things, control operation of the linear drive system 110.

The linear drive system 110 includes a lead screw 114, and a gap set motor and encoder 116. The lead screw 114 is connected to the rheometer head assembly 108 such that rotation of the lead screw 114 causes linear displacement of the rheometer head assembly 108 relative to the frame 102. The processing and control electronics 112 are in electrical communication with, and control operation of, the gap set motor and encoder 116. The processing and control electronics 112 are configured to deliver an electrical signal to the gap set motor and encoder 116 to control rotation of the lead screw 114, and thereby control movement of the rheometer head assembly 108 relative to the frame 102.

Figure 1B:
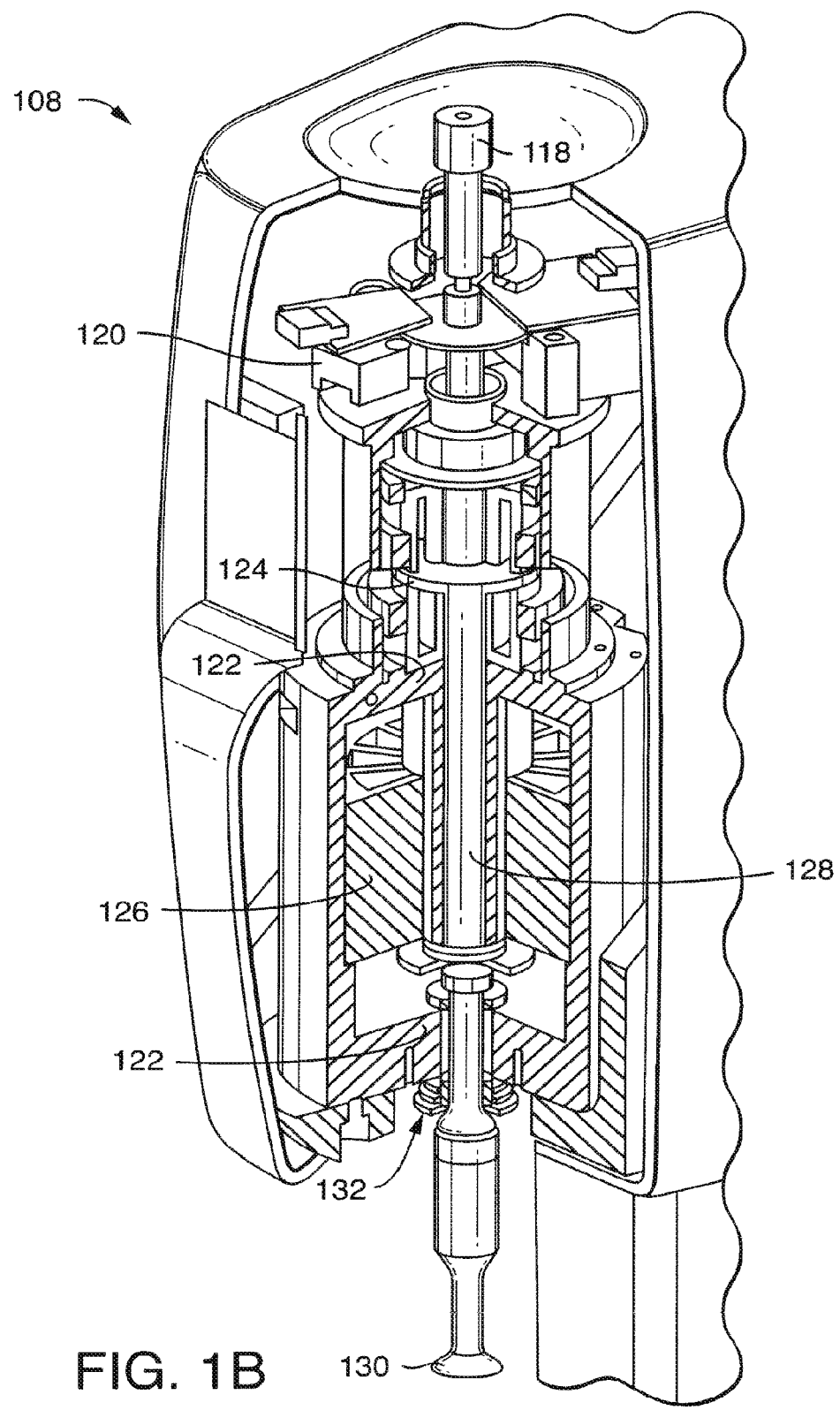
FIG. 1B is schematic perspective view of a rheometer head assembly from the rotary rheometer of FIG. 1A.

Referring to FIG. 1B, the rheometer head assembly 108 includes a draw rod 118, an optical encoder 120, a pair of radial air bearings 122, a magnetic thrust bearing 124, a drag cup motor 126, and a drive shaft 128. A second measuring object 130 (shown as a parallel plate) is mounted to a distal end portion of the drive shaft 128.

The processing and control electronics 112 (FIG. 1A) provide an electrical current to the drag cup motor 126, which generates and applies a torque to the drive shaft 128. The torque in the drive shaft 128, in turn, applies torque to the second measuring object 130. The optical encoder 120 is in electrical communication with the processing and control electronics 112, and is configured to measure the angular displacement and/or angular velocity of the second measuring object 130. The radial air bearings 122 provide the drive shaft 128 with stiffness and support in the radial direction, and the thrust bearing 124 provides stiff, axial support for the drive shaft 128.

For obtaining accurate measurements, a measurement gap of fixed dimension should be maintained between the first and second measuring objects 104, 130. The measurement gap being the spacing between the first and second measuring objects 104, 130 in which a material to be examined is received. Thermal expansion of the motor drive shaft 128 due to heat generation within the motor can change (i.e., increase or reduce) the measurement gap. In this regard, a position sensor 132 is provided near an end of the drive shaft 128 that connects to the second measuring object 130. The position sensor 132 is configured to measure expansion of the drive shaft 128. The measured expansion can then be used to adjust the position of the second measuring object 130 relative to the first measuring object 104 so as to maintain a fixed (constant) measurement gap therebetween.

As shown in FIG. 1C, the position sensor 132 is an inductive linear position sensor that includes a target 134 that is mounted circumferentially about a distal end portion of the drive shaft 128. The target 134 can be formed of metal, e.g., aluminum. The position sensor 132 also includes a coil former 136, which can be formed of a plastic material, and a pair of electrically conductive coils 138, which are wound about the coil former 136. The coil former 136 is mounted to the drag cup motor 126. The coils 138 are in electrical communication with the processing and control electronics 112. The processing and control electronics 112 provide a high frequency signal to the coils 138 and measure impedance in the coils 138. The high frequency signal in the coils 138 sets up eddy currents in the target 134. When the target is centered between the coils 138, the impedance in the coils 138 is balanced. However, movement of the drive shaft 128 due to thermal expansion causes the target 134 to be displaced relative to the coils 138, which, in turn, causes a difference in impedance in the coils 138. The processing and control electronics 112 can correlate the impedance change to a corresponding change in the measurement gap and can adjust the position of the second measuring object 130 relative to the first measuring object 104 via operation of the linear drive system 110.

In use, a material to be examined is disposed between the first and second measuring objects 104, 130. Then, the rheometer head assembly 108 is displaced relative to the frame 102 to establish a pre-determined measurement gap between the first and second measurement objects 104, 130. The displacement of the rheometer head assembly 108 can be controlled via the processing and control electronics 112, as discussed above. Shear force is applied, under controlled temperature conditions, to the material via relative movement of the second measuring object 130 relative to the first measuring object 104. The processing and control electronics 112 monitor the impedance of the coils 138 of the position sensor 132 to detect thermal expansion of the drive shaft 128. Impedance change is related to gap change and gap change can be corrected in real time. In this regard, if the measured impedance indicates thermal expansion of the drive shaft 128 and a corresponding change in the measurement gap, then the position of the second measuring object 130 relative to the first measuring object 104 is adjusted, via displacement of the rheometer head assembly 108 relative to the frame 102, to re-establish the pre-determined measurement gap.

Although a few implementations have been described in detail above, other modifications are possible. For example, while an implementation of a rheometer has been described in which the rheometer head assembly and the associated, second measuring object is displaceable relative to frame, in some cases, the first measuring object may, alternatively or additionally, be displaceable relative to the frame and/or relative to the second measuring device to control the measurement gap.

Accordingly, other implementations are within the scope of the following claims.

What is claimed is:

1. A method of maintaining a measurement gap in a rheometer, the method comprising:
   delivering a high frequency signal to a pair of coils, thereby to set up eddy currents in a target disposed between the coils;
   measuring impedance in the coils thereby to detect a displacement of the target relative to the coils corresponding to thermal expansion of a drive shaft; and
   automatically adjusting a position of a first measuring object relative to a second measuring object to maintain a substantially constant measurement gap therebetween.

2. The method of claim 1, wherein the target is mounted to the drive shaft.

3. The method of claim 1, wherein the pair of coils is disposed circumferentially about the drive shaft and axially spaced apart from one another.

4. The method of claim 1, wherein the first measuring object is supported by a frame.

5. The method of claim 1, wherein the second measuring object is supported by the drive shaft.

* * * * *